United States Patent
Johnson et al.

(10) Patent No.: US 7,035,681 B2
(45) Date of Patent: Apr. 25, 2006

(54) COLONOGRAPHY OF AN UNPREPARED COLON

(75) Inventors: C. Daniel Johnson, Rochester, MN (US); Matthew R. Callstrom, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 10/253,673

(22) Filed: Sep. 24, 2002

(65) Prior Publication Data

US 2003/0023163 A1 Jan. 30, 2003

Related U.S. Application Data

(63) Continuation of application No. 09/522,389, filed on Mar. 10, 2000, now Pat. No. 6,477,401.

(51) Int. Cl.
*A61B 5/05* (2006.01)

(52) U.S. Cl. ............ 600/420; 600/407; 600/410; 600/424; 600/431; 600/458; 424/9.51; 424/9.52

(58) Field of Classification Search ........ 600/407–436, 600/458; 424/9.51–9.52
See application file for complete search history.

(56) References Cited

U.S. PATENT DOCUMENTS

| | | | | |
|---|---|---|---|---|
| 3,915,152 A * | 10/1975 | Colonna | .................... | 600/433 |
| 5,322,070 A * | 6/1994 | Goodman et al. | .......... | 600/560 |
| 5,782,762 A * | 7/1998 | Vining | ........................ | 600/407 |
| 6,477,401 B1 * | 11/2002 | Johnson et al. | ............. | 600/431 |

* cited by examiner

*Primary Examiner*—Brian L. Casler
*Assistant Examiner*—William Jung
(74) *Attorney, Agent, or Firm*—Faegre & Benson LLP

(57) ABSTRACT

A method for generating colonography images for colorectal screening of a patient. The patient is administered an amount of radiopaque stool marker which will enable stool present in the patient's colon to be distinguished from soft tissue. The patient's colon is imaged after the stool marker has been administered to generate colonography images. Preparation of the colon is simulated by processing the colonography images to remove marked stool before the images are observed during a diagnosis session.

20 Claims, 22 Drawing Sheets

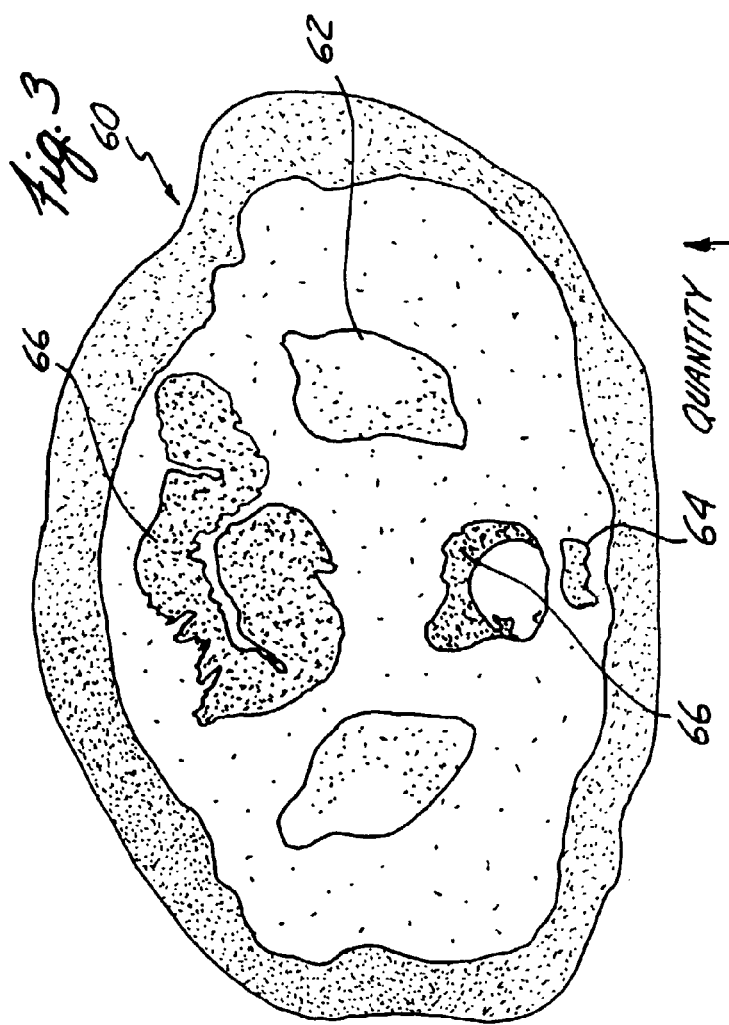
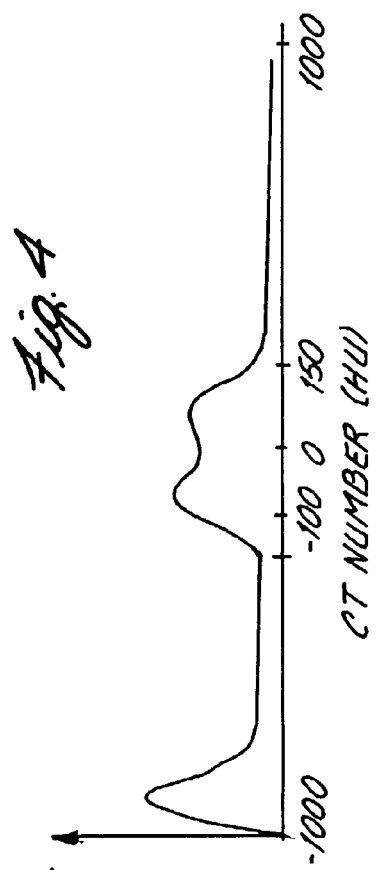

Study Groups
Frequency and Period of Dilute Barium Sulfate

| Group | Period | Dose | No. pts |
|---|---|---|---|
| 1 | 24 h | 2 | 6 |
| 2 | 24 h | 5 | 11 |
| 3 | 48 h | 4 | 18 |
| 4 | 48 h | 6 | 14 |
| 5 | 48 h | 7 | 8 |

Stool Labeling Scoring

- Threshold for marking set at 150 HU

0 = equal to background
1 = 1 - 25%
2 = 25 - 50 %
3 = 50 - 75 %
4 = 75 - 100%

Stool Labeling Scoring
- Scoring = 0 (equal to background)
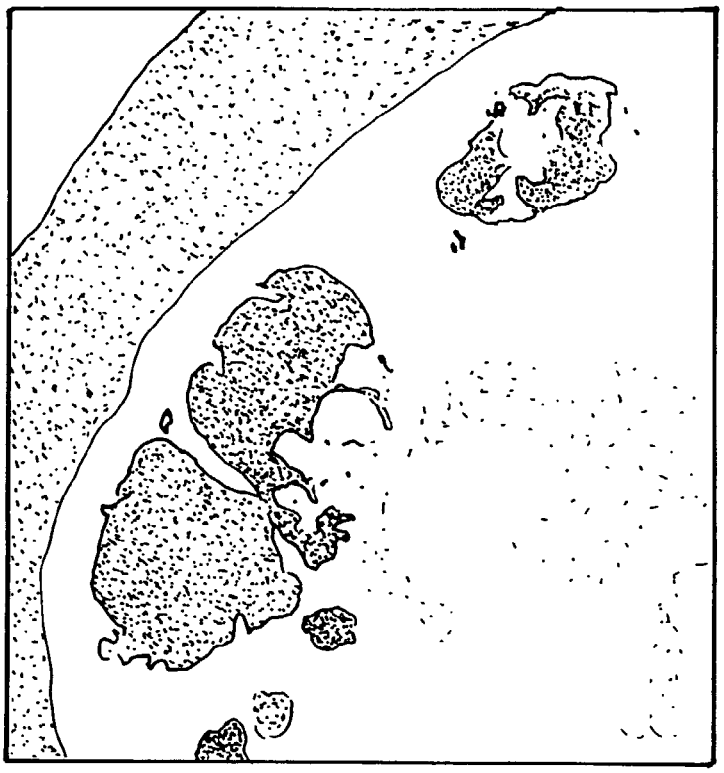
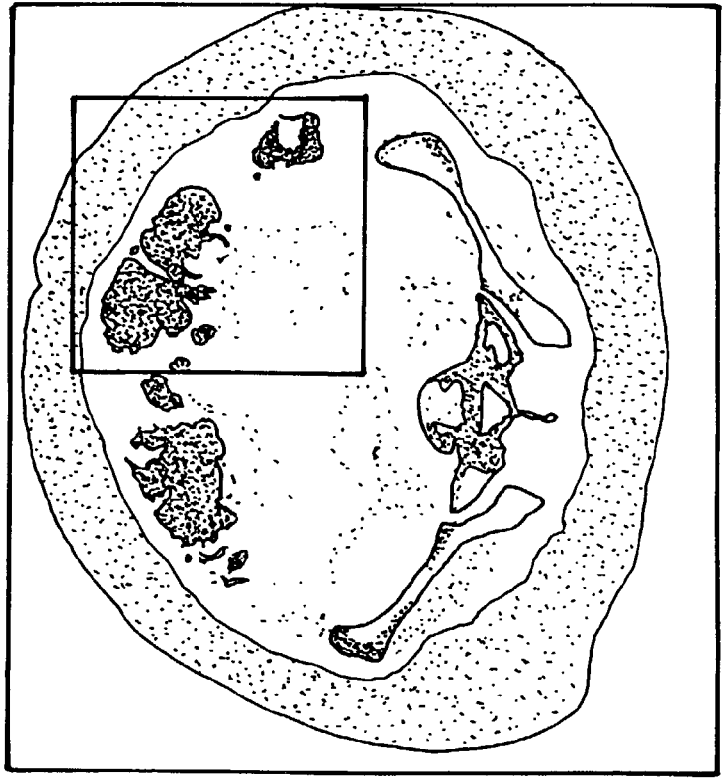
Fig. 16

Stool Labeling Scoring
- Scoring = 1 (5 - 25%)
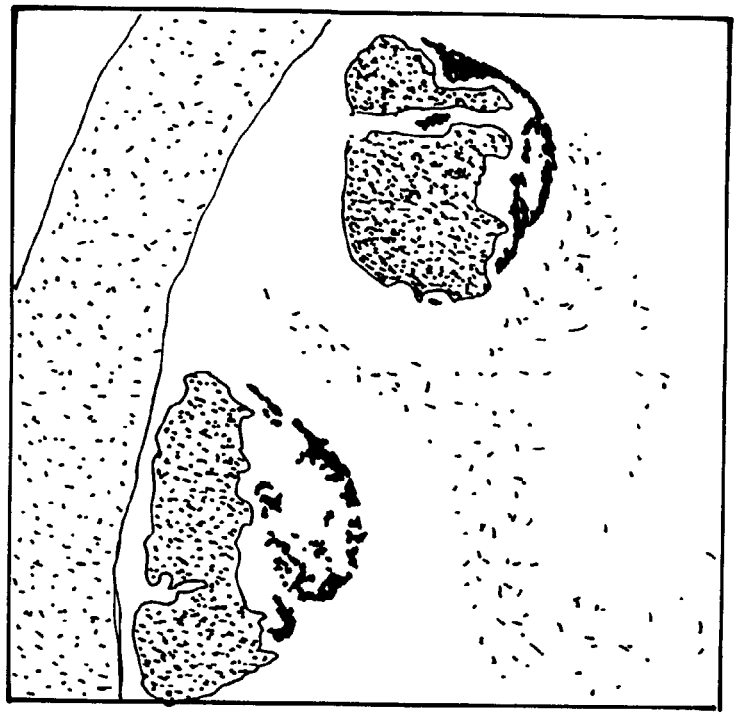
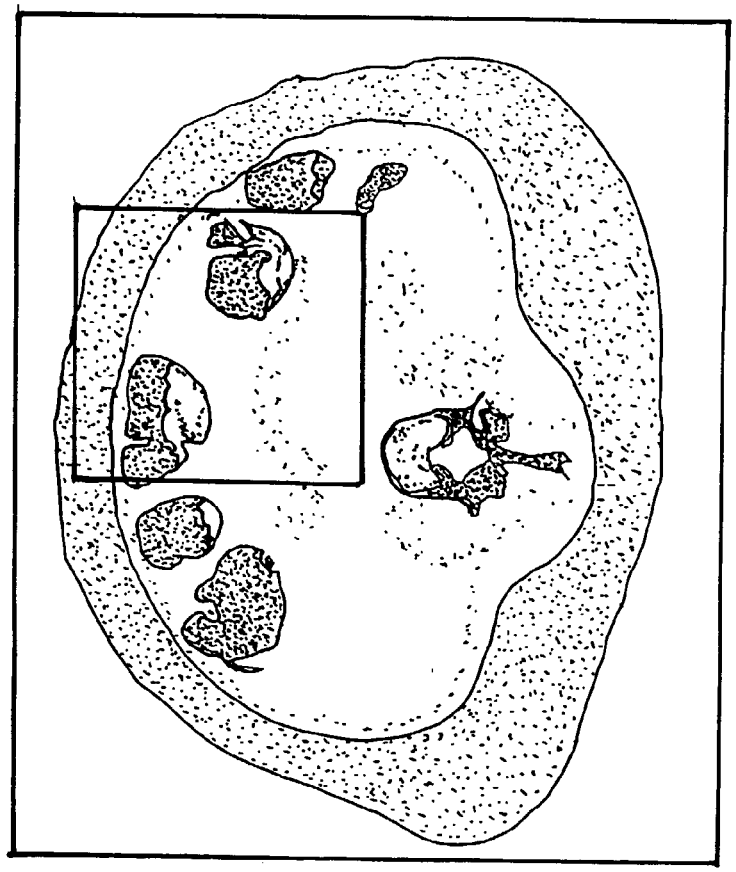
Fig. 17

Stool Labeling Scoring

- Scoring = 2 (25 - 50%)

Stool Labeling Scoring

- Scoring = 3 (50 - 75%)

Stool Labeling Scoring
- Scoring = 4 (75 - 100%)
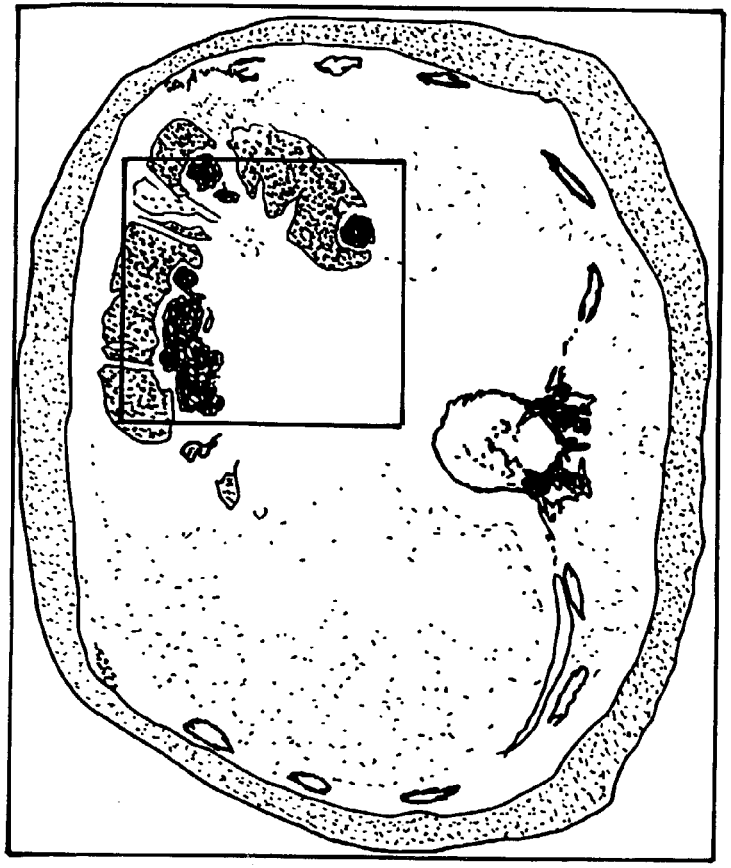
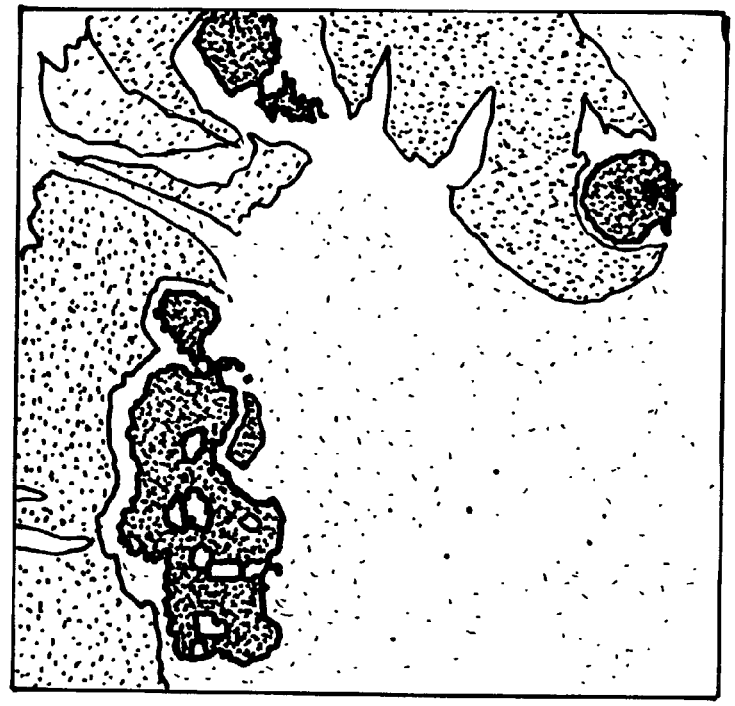
Fig. 20

COLONOGRAPHY OF AN UNPREPARED COLON

REFERENCE TO RELATED APPLICATION

This application is a Continuation of Ser. No. 09/522,389 filed on Mar. 10, 2000, which became U.S. Pat. No. 6,477,401.

FIELD OF THE INVENTION

The present invention relates generally colonography (also known as computed tomographic colonography or CTC), a minimally invasive imaging technique for colorectal cancer screening. In particular, the invention is a method for generating colonography images that does not require cathartic preparation of the colon prior to the imaging.

BACKGROUND OF THE INVENTION

Colonography, the use of electronic imaging technologies such as computed tomography (CT) to generate images of a patient's colon for purposes of colorectal cancer screening, is generally known. Descriptions of this diagnostic methodology can, for example, be found in the Johnson et al. U.S. Pat. No. 5,891,030, the Johnson et al. PCT publication WO 98/32371, the Vining U.S. Pat. No. 5,782,762 and the Vining et al. U.S. Pat. No. 5,920,319, all of which are hereby incorporated by reference. Briefly, this methodology involves obtaining a series of CT images of adjacent portions or slices of the colon. A radiologist then studies each of the images to identify any pre-cancerous polyps. Also known as virtual colonoscopy, this technique effectively creates a computer simulated intraluminal flight through the colon. This dynamic diagnostic methodology has been demonstrated to be a highly efficacious approach for detecting colorectal polyps.

Although these known colonography approaches are generally much less invasive and more comfortable for the patient that other colorectal cancer screening techniques such a colonoscopy, they still require that the patient's colon be prepared (i.e., cleansed of stool) through the use of laxatives or other cathartics. Removal of the stool is required because the stool exhibits the same density to the imaging processes as the polyps and soft colon tissue. In other words, the stool looks very similar to polyps and the tissues of the colon in the colonography images. The presence of stool can therefore mask polyps and other features in the images that may be relevant to the diagnostic process. Unfortunately, these colon preparation processes can be time consuming and uncomfortable for the patient. Patient compliance with the preparation processes is sometimes therefore poor, resulting in reduced efficacy of the diagnostic procedure. Perhaps even worse, some patients may forego the diagnostic procedure altogether to avoid the inconvenience of the preparation process.

It is evident that there is a continuing need for improved colonography methodologies. In particular, there is a need for colonography methodologies that are less sensitive to the need for thorough colon preparation prior to imaging. A methodology that does not require substantial preparation would be particularly desirable. To be viable, any such method must be highly efficacious and efficient to perform. A colonography approach which meets these objectives could enhance patient acceptance of the diagnostic procedure and reduce the morbidity of colorectal cancer.

SUMMARY OF THE INVENTION

The present invention is a highly efficacious and convenient method for generating colonography images for colorectal cancer screening. One embodiment of the invention includes administering to the patient an amount of stool marker which will enable stool present in the patient's colon to be distinguished from soft tissue. The stool marker can be administered in liquid or pill form. Following administration of the stool marker, the patient's colon is imaged to generate the colonography images. The colonography images are then processed to mark or remove the marked stool and simulate the preparation of the colon. The images can then be displayed to a radiologist during a diagnosis session.

BRIEF DESCRIPTION OF THE DRAWINGS

FIG. 3 is an image of a cross section of a patient's abdomen taken by a CT scanner.

FIG. 4 is a graph of the distribution of the pixel intensity values (on the Houndsfield scale) of the image shown in FIG. 3.

FIG. 12 is a chart describing generally the barium sulfate administration schedule or protocol during a test of the invention on a group of patients.

FIG. 15 is an illustration of the scoring system used to quantify the amount of stool in the colons that was adequately marked by the associated administration protocol during the test.

FIG. 16 is a CT image of a cross section of an abdomen including portions of a colon, and a detailed CT image of a portion of the colon, illustrating an example of the type of marking that would be assigned a score of 0 in the test.

FIG. 17 is a CT image of a cross section of an abdomen including portions of a colon, and a detailed CT image of a portion of the colon, illustrating an example of the type of stool marking that would be assigned a score of 1 in the test.

FIG. 20 is a CT image of a cross section of an abdomen including portions of a colon, and a detailed CT image of a portion of the colon, illustrating an example of the type of stool marking that would be assigned a score of 4 in the test.

DETAILED DESCRIPTION OF THE PREFERRED EMBODIMENTS

The present invention is a method for performing colonography which involves marking the stool present in the patient's colon with a radiopaque material before the colon is imaged. The marked stool can then be electronically identified and effectively removed from the images before the images are presented to a radiologist in a diagnostic session. In effect, the method is capable of providing simulated colon preparation and stool recognition. Highly efficacious colonography diagnostic procedures can therefore be performed without subjecting the patient to uncomfortable preparation processes.

Figure 1:
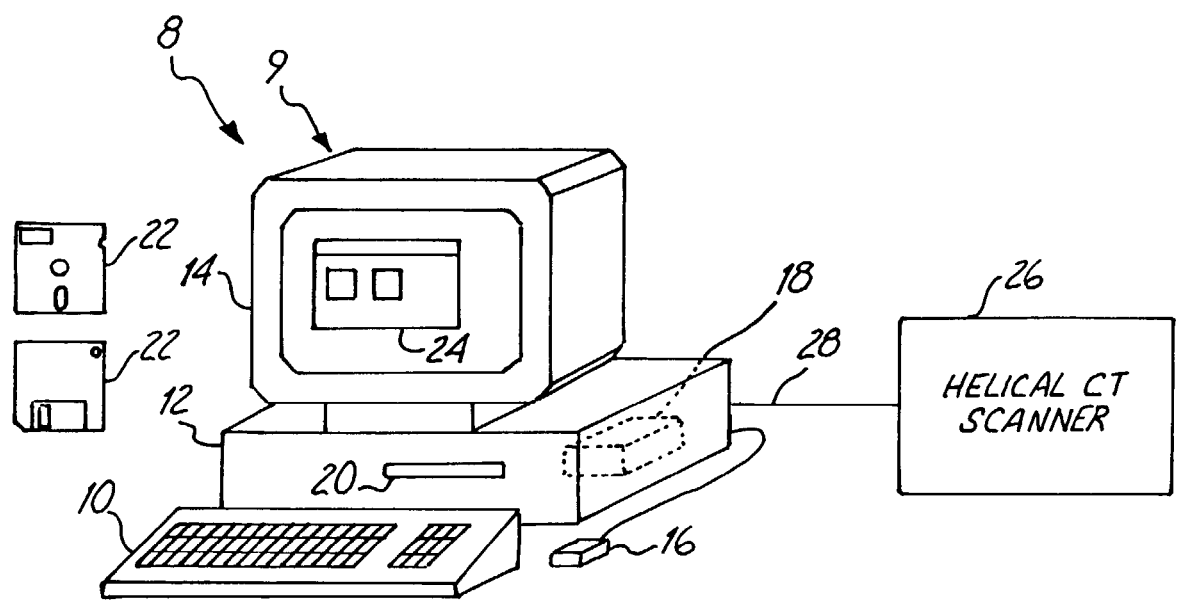
FIG. 1 is a diagrammatic illustration of a computed tomographic (CT) workstation which can be used in connection with the colonography method of the present invention.

FIG. 1 is an illustration of a computed tomographic (CT) imaging system 8 which can be configured to implement the colonography methodology of the present invention. As shown, the system 8 includes a workstation 9 having a computer 12 and user-actuated input/output devices such as keyboard 10 and mouse 16. Computer 12 includes a processor (not separately shown), memory 18 and storage device 20 for reading and writing data to removable storage media 22 such as compact disk read only memory (CD ROM) or floppy disks. Programmed instructions (e.g., software) for performing the image processing algorithms of the invention described below, as well as other conventional aspects of colonography system, can be stored in the memory 18 and executed by the processor. Computer 12 can be coupled to other input/output devices (not shown) such as a local area network (LAN) or wide area network (WAN) through an interface cable (not shown). The system 8 also includes a display device such as monitor 14 which can be used to display the colonography images 24 to a radiologist during a diagnostic session. The radiologist can scroll through the images 24 and otherwise control the display of the images through the use of keyboard 10 and/or mouse 16 in connection with a graphical user interface (not shown) on monitor 14. System 8 is connected to an imaging instrument such as CT scanner 26 through an external data bus 28. Prototypes of the invention have been developed using images generated by a commercially available General Electric Light Speed model CT scanner. However, other CT scanners, as well as other imaging technologies such as electron beam tomography (EBT), magnetic resonance imaging (MRI), positron emission tomography (PET) and high resolution ultrasound can also be used in connection with the invention.

Figure 2:
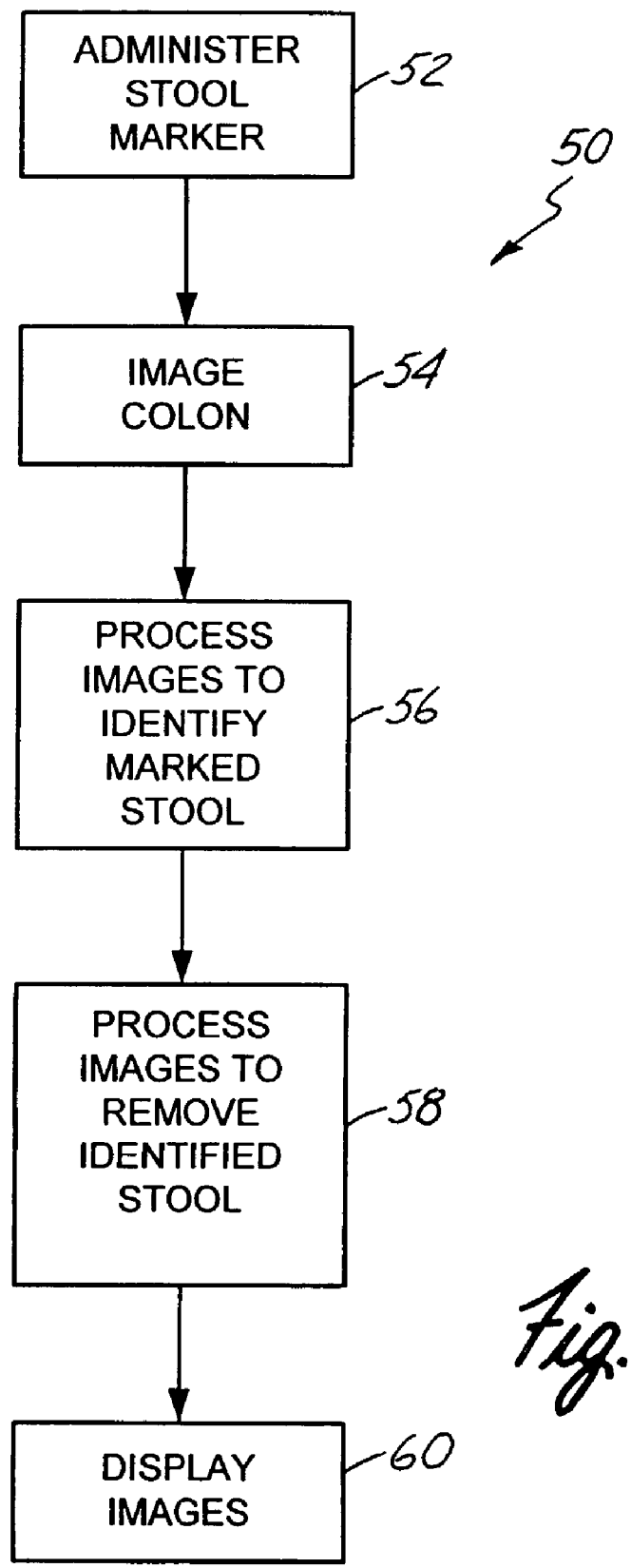
FIG. 2 is a flowchart describing generally the colonography method of the present invention.

FIG. 2 is a flow chart illustrating generally the colonography method 50 of the present invention. As shown, the method 50 includes the administration of a stool marker to the patient (step 52) followed by the imaging of the patient's colon (step 54). The colonography images produced during step 54 are then electronically processed to identify the marked stool (step 56). The marked stool is preferably electronically removed from the colonography images (step 58), and the removed stool replaced with an image representation of air or other feature (step 60). The processed colonography images are then displayed for a diagnostic session by a radiologist (step 62).

The stool marker administered to the patient at step 52 is a compound or other substance which can be electronically identified in the colonography images. In general, the stool marker will be opaque to the wavelength of radiation or other parameter (e.g., ultrasound) used by the imaging instrument to generate the colonography images. Preferably, the stool marker has a density or other image-responsive characteristic which is sufficiently different than the density of stool and soft tissues of the colon, and from air or other gas or substance within the colon being imaged, to enhance the ability of the image processing algorithm and/or a visual observer to efficiently and accurately distinguish the stool marked with the marker from the polyps and other tissues of the colon. Other desirable characteristics of the stool marker are its ability to completely mix with the stool present throughout the length of the colon being imaged, and its tendency to not coat the colon wall. Thorough and homogeneous mixing with stool throughout the colon enhances the capability of the imaging processing algorithm to maximize the identification of stool. The ability of the processing algorithm (or a radiologist visually observing the images) to distinguish between the marked stool and the colon tissues will be enhanced if the amount of marker on the colon walls is minimized. As described in greater detail below, orally consumed doses of liquid suspended barium sulfate (which is radiopaque to CT imaging processes) administered over a period of twenty-four to forty-eight hours immediately prior to the colon imaging step 54 was used as a stool marker and associated protocol during tests of the invention.

Barium sulfate or other stool marker can also be administered in pill form. By way of example, the stool marker can be in tablet form, coated tablet form or enclosed in a capsule. The pill form of the stool marker can be formulated to cause the effective release of the stool marker in the stomach of the patient following its administration. Pill form stool markers will enhance patient compliance with the administration of the stool marker by reducing any unpleasant taste of other effects associated with the consumption of the marker.

The colon imaging step 54 is performed in a conventional manner such as those described in the patent documents identified in the Background of the Invention section. Preferably, the set of colonography images generated at step 54 are three dimensional (3D) images. Commercially available software programs such as VoxelView from Vital Images can be used for this purpose. Alternatively, efficacious colorectal screening diagnoses can be obtained through the use of two dimensional (2D) colonography images processed in accordance with the methodology described herein.

FIG. 3 is an illustration of a CT colonography image of a cross section of a patient's abdomen 60. Visible in the image of abdomen 60 are the bones of the patients pelvis 62 and spine 64, as well as portions of the colon 66. The images such as that shown in FIG. 3 which are viewed by the radiologist are typically gray-scale images with the most dense tissue (e.g., bone and marked stool) and other substances represented by the lightest intensity shades (i.e., white) and the least dense tissue and other substances (e.g., air) represented by the darkest intensity shades (e.g., black). In this convention, the bones of pelvis 62 are shown as being white in the image, and the air within colon 66 shown as being black. The intensity of the individual pixels of the images are represented by digital pixel intensity values which can be processed by the computer 12 (FIG. 1). CT images such as that shown in FIG. 3 use what is known as the Houndsfield scale to represent the range of pixel intensity values. On the Houndsfield scale a value of −1000 houndsfield units (HU) is used to represent the density of air and a value of 0 HU to represent water. Bone will generally have densities corresponding to between 500 and 1000 HU.

FIG. 4 is a graph of the number or distribution of the pixel intensity values in the image of abdomen 60 across the Houndsfield scale. As shown, there is a concentration of pixel values around −1000 HU near the lower end of the scale, and a concentration of pixel values between approximately −100 and 150 HU. The concentration of the pixel values around −1000 HU generally represents the volume of air in the image (including that within the colon 66). The concentration of the pixel values centered at about −100 HU generally represents fat. The concentration of the pixel values centered at about 50 HU generally represents muscle and other soft tissues such as unmarked stool and those of the colon wall. Portions of the image represented by pixel intensity values greater than about 150 HU are generally bone or marked stool.

Figure 6:
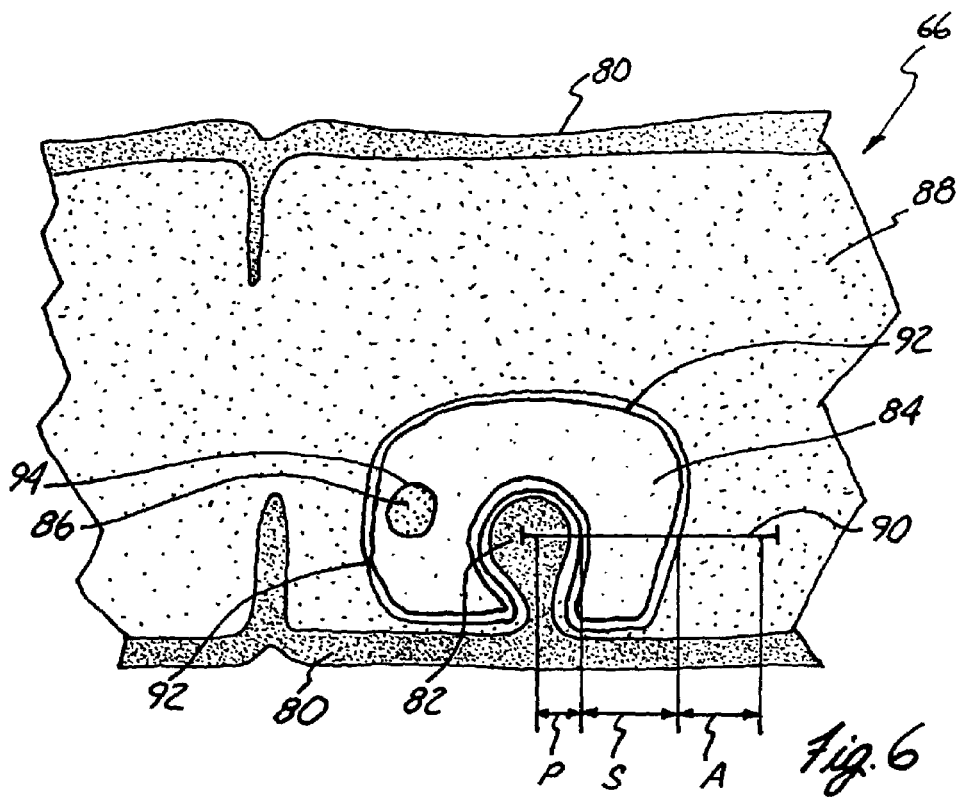
FIG. 6 is a detailed image of a portion of the colon shown in FIG. 3.

FIG. 6 is an illustration of a portion of a CT image of a colon 66 having a wall 80 and a polyp 82 extending from the wall. A section of marked stool 84 is present within the colon 66 and surrounds the polyp 82. Present within the marked stool 84 is a section of unmarked stool 86. The air 88 within the colon 66 is the least dense and therefore darkest portion of the image. The marked stool 84 is the most dense and therefore lightest portion of the image. The tissues of the colon wall 80 and the unmarked stool 86 have a density and therefore gray-scale shade which is between those of the air 88 and marked stool 84.

Figure 7:
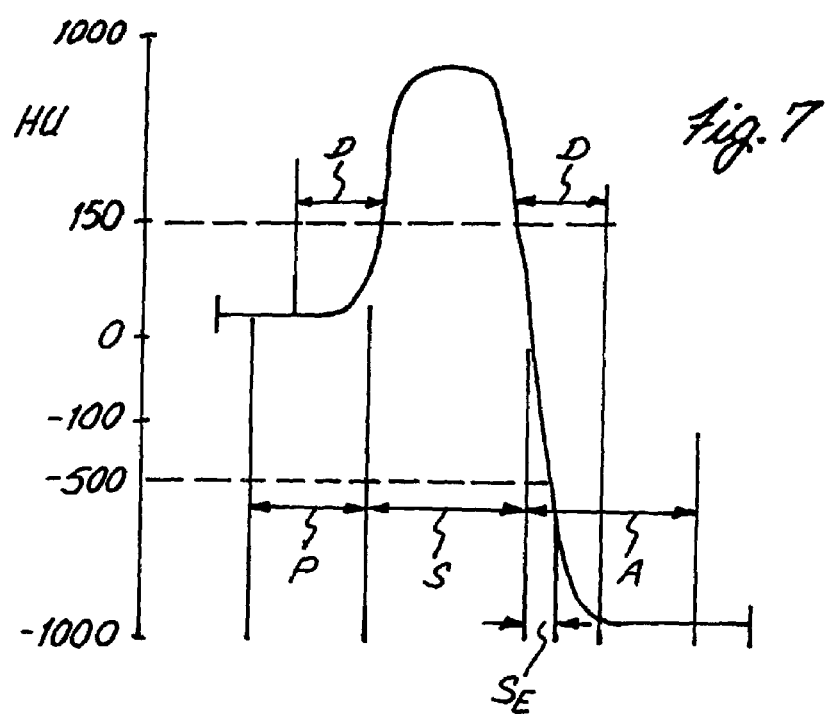
FIG. 7 is a graph of the pixel intensity values (not to scale) of a portion of one of the rows of pixels of the image shown in FIG. 6.

FIG. 7 is a graph (not to scale) of the intensity values (in HU) of the pixels along the portion of row 90 in the image shown in FIG. 6. As shown, the pixels of the row 90 include a group P which extends through the polyp 82, a group S which extends through the marked stool 84 and a group A which extends through the air 88 within the colon 66. The pixels of the polyp group P have intensity values in the range of 50 HU. The pixels of the marked stool group S have intensity values in the range of 900 HU. The pixels of the air group A have intensity values in the range of −900 HU.

Figure 5:
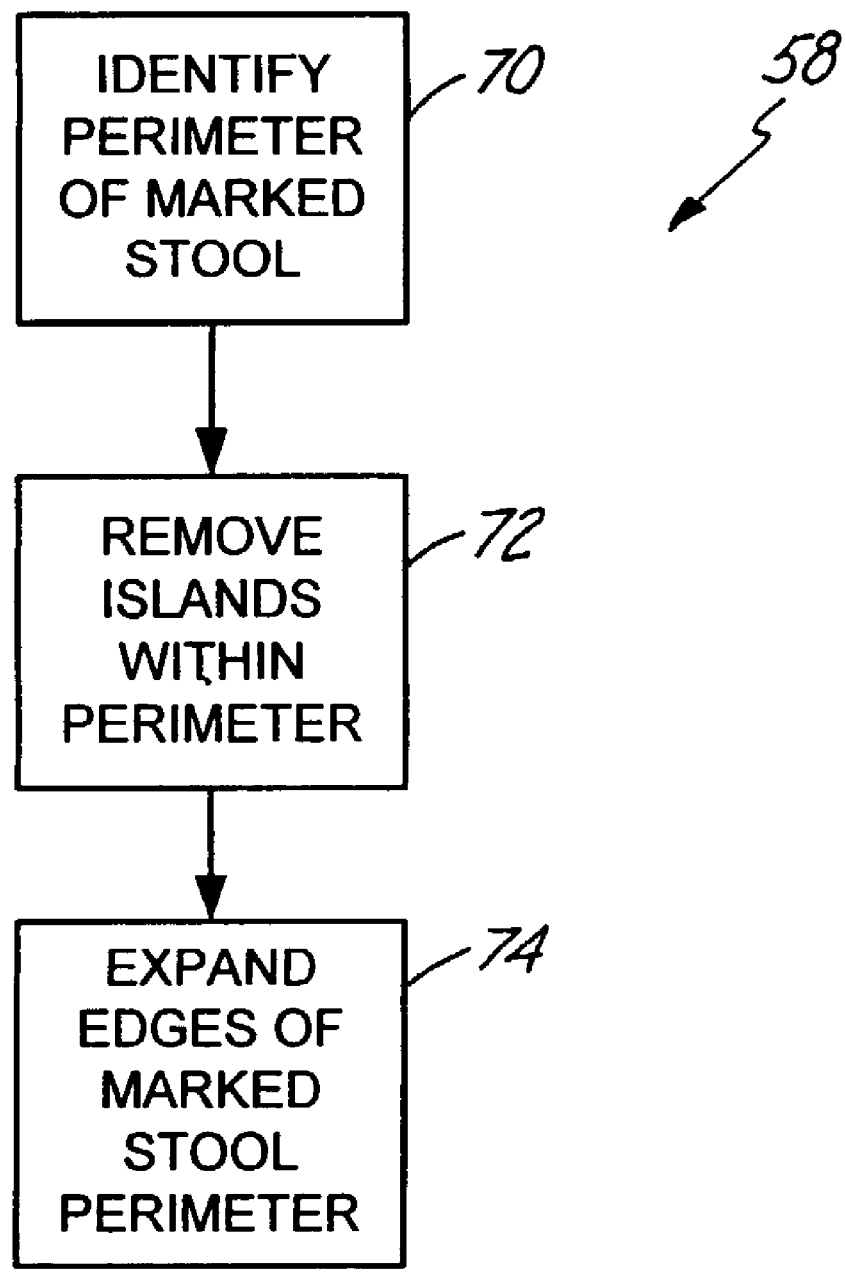
FIG. 5 is a flowchart describing the marked stool identification step shown in FIG. 2.

The digital image processing methods used to perform marked stool identification step 56 (FIG. 2) during the tests of the invention described below generally include the three steps illustrated in FIG. 5: 1) marked stool perimeter identification step 70; 2) island removal step 72; and 3) perimeter edge expansion step 74. The marked stool perimeter identification step 70 is performed by a thresholding operation. The thresholding operation makes use of a marked stool threshold value which is selected as the minimum pixel intensity value representative of marked stool. The marked stool threshold value can be selected to optimize the identification of marked stool on the basis of a variety of factors including the type of stool marker used, the quality of the stool marking procedure on a given patient and imaging parameters. A marked stool threshold value of 150 HU was used during the tests of the invention described below. Pixels having intensity values greater than 150 HU are designated as those representing marked stool in the image, while pixels having intensity values less than or equal to 150 HU are designated as representing other features of the image (e.g., air 88, unmarked stool 86 and the colon wall 80).

During the marked stool perimeter identification step 70, the pixel intensity values of the image are compared to the marked stool threshold value to determine whether they represent marked stool 84 or other image features such as colon wall 80. The result of this thresholding operation is data representing a map of areas of the image representative of marked stool 84. The locations of the edges or perimeters of the areas of marked stool 84 can then be identified. In the image shown in FIG. 6, for example, the outer perimeter 92 of the marked stool 84 can be identified, as well as the inner perimeter 94 of the volume of unmarked stool 86 within the marked stool.

Figure 8:
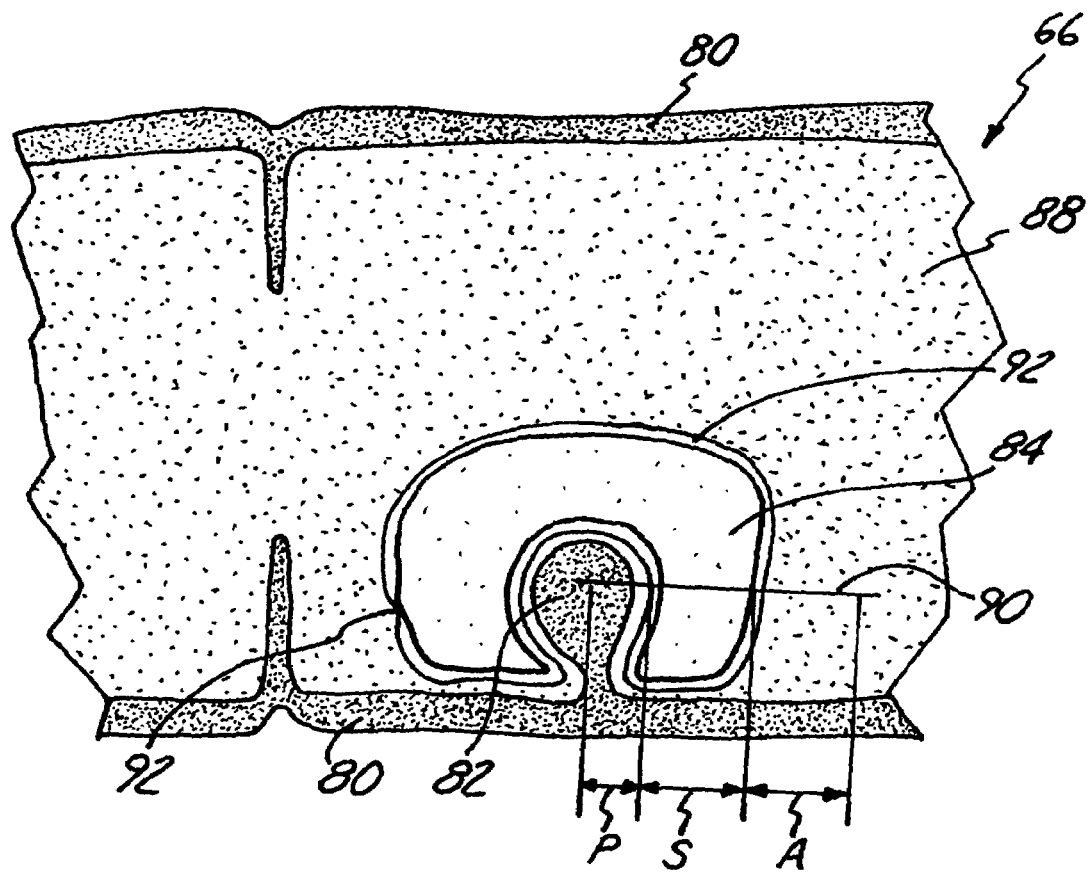
FIG. 8 is an image of the portion of the colon shown in FIG. 6 following the removal of the island of unmarked stool.

During the island removal step 72, all features of the image such as the unmarked stool 86 which have been identified as representing something other than marked stool 84, and which are completely surrounded by the marked stool (i.e., are within the perimeter 92), are "removed" from the image. This removal operation is performed because the completely surrounded volume is presumed to represent features of the image other than the colon wall 80 or polyp 82. In the image shown in FIG. 6, the polyp 82 would not be removed from the image since it is attached to the colon wall 80 and not completely surrounded by the marked stool 84. In one embodiment of the invention, island features such as unmarked stool 86 which are removed from the image are replaced with pixel values representing marked stool. FIG. 8 is an illustration of the image corresponding to that in FIG. 6 after the island of unmarked stool 86 has been removed and replaced with pixel intensity values corresponding to the marked stool 84.

As shown in FIGS. 6 and 7, the intensity values of the pixels at the perimeter 92 of the marked stool 84 do not shift immediately between values representative of marked stool and those representative of other features such as air 88. Instead, there is an edge transition distance at the perimeter 92 over which the range of pixel intensity values change. The edge transition distance is due to a number of factors including the relatively low quantity of marked stool 84 at the perimeter 92. It has been observed that the perimeters 92 identified during the step 70 described above (i.e., the initially identified perimeter) can sometimes be insufficient to represent the actual perimeter of the identified area of marked stool 84.

Perimeter edge expansion step 74 is performed to effectively sharpen the edge and enhance the accuracy of the identification of the initially identified perimeter 92 of marked stool 84. Briefly, the edge expansion step 74 determines whether the perimeter 92 is adjacent to the air 88 within the colon 66, or adjacent to soft tissues such as wall 80 or polyp 82. The identified perimeter 92 of the marked stool is then conditionally expanded based on the determination. If it is determined that the perimeter 92 is adjacent to air 88 within the colon 66, the identified perimeter is expanded to include pixels having intensity values less than the marked stool threshold value on the basis that they represent unmarked stool rather than other features such as the colon wall 80 or polyp 82. Conversely, if it is determined that the perimeter 92 is adjacent to walls 80 or polyp 82, the identified perimeter is not expanded on the basis that the pixels adjacent to the initially identified perimeter represent the colon walls or polyps rather than unmarked stool.

The edge expansion step 74 makes use of an expansion distance threshold value and an air intensity threshold value. The expansion distance threshold is a distance, in terms of number of pixels, beyond the initially identified perimeter 92 which is evaluated to identify other features such as air 88, colon walls 80 and polyps 82 adjacent to the perimeter. In the tests of the invention described below, the expansion distance threshold was set at a number of pixels which corresponds generally to a distance of 2–3 mm. Other values can be used for the expansion distance threshold to optimize the edge expansion step 74 for particular applications and algorithms.

The air intensity threshold value is a pixel intensity value, in HU, which is selected as the maximum pixel intensity value representative of air 88 within the colon 66. The air intensity threshold value can be selected to optimize the identification of air 88 from other features such as unmarked stool on the basis of a variety of factors including the type of stool marker used, the quality of the stool marking procedure on a given patient and imaging parameters. An air intensity threshold value of −500 HU was used during the tests of the invention described below. Pixels having intensity values less than −500 HU are designated as those representing air in the image, while pixels having intensity values greater than or equal to −500 HU are designated as representing other features of the image (e.g., unmarked stool and the colon wall 80).

Figure 9:
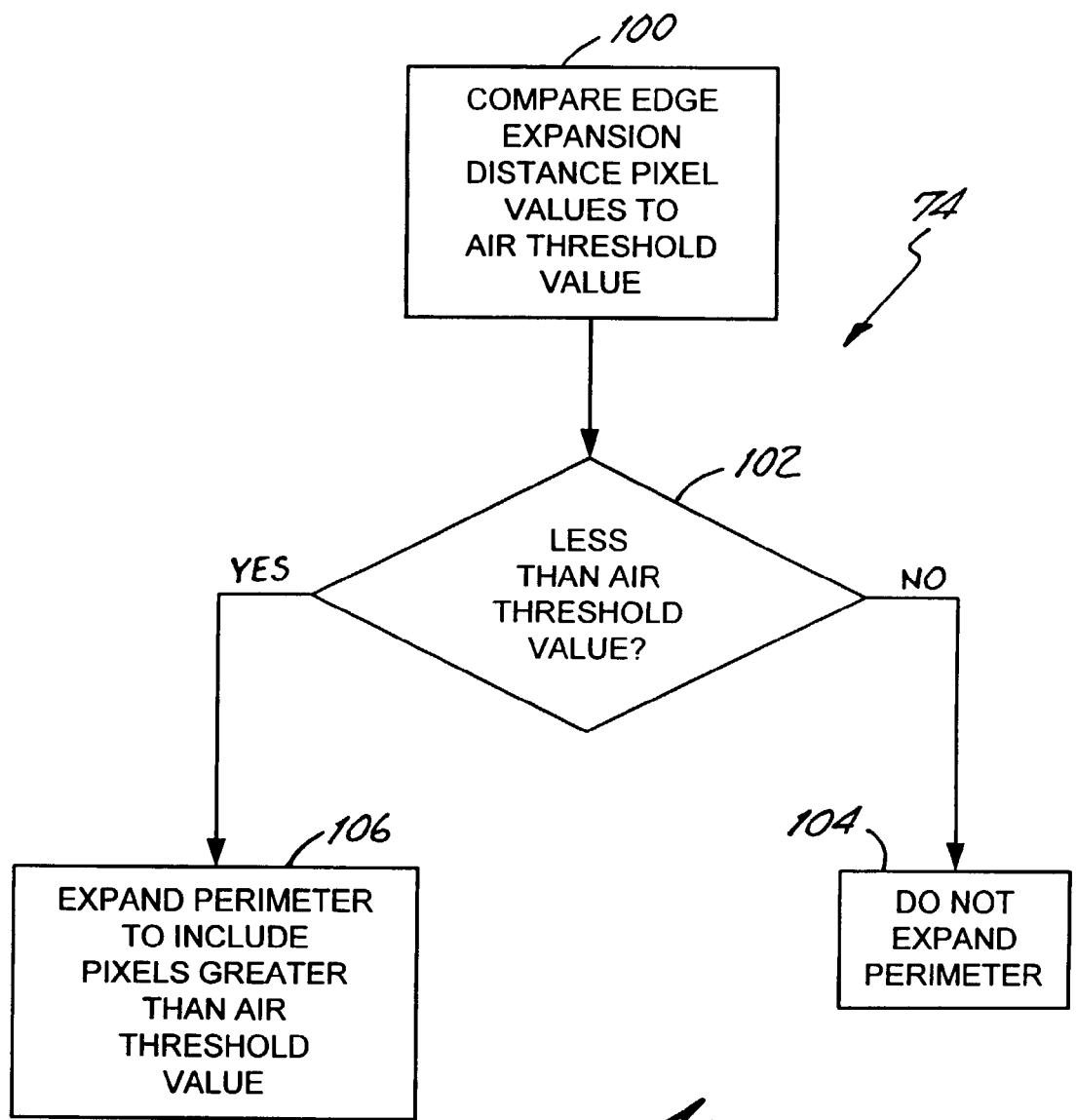
FIG. 9 is a flowchart describing the marked stool perimeter expansion step shown in FIG. 5.

FIG. 9 is a flowchart which generally describes the digital image processing methods which can be used to perform the edge expansion step 74. As shown, the intensity values of the pixels within the expansion distance threshold and beyond the initially identified perimeter 92 are compared to the air intensity threshold value at step 100. If it is determined that the pixel intensity values within the expansion distance threshold are greater than or equal to the air intensity threshold value at step 102, the initially identified perimeter 92 is not expanded as indicated by step 104. This sequence of steps 100, 102 and 104 can be illustrated with reference to FIGS. 6 and 7. In these Figures the pixels of stool group S all have intensity values greater than 150 HU. The pixels of the polyp group P that are within the expansion distance threshold D of the stool group S all have intensity values which are greater than an air intensity threshold value of −500 HU. Accordingly, the initially identified perimeter 92 of the marked stool 84 is not expanded at the interface between the pixels of the polyp group P and stool group S in the row 90.

If it is determined that pixel intensity values within the expansion distance threshold are less than the air intensity threshold value at step 102, the initially identified perimeter 92 is expanded as indicated at step 106. In the embodiment described in FIG. 9, the distance of the expansion is equal to the number of pixels within the expansion distance threshold that have intensity values greater than the air threshold value. This sequence of steps 100, 102 and 106 is also illustrated in FIGS. 6 and 7. In these Figures the pixels of the air group A that are within the expansion distance threshold D of the stool group S include pixels which are less than the air intensity threshold value of −500 HU. Accordingly, the initially identified perimeter 92 of the marked stool 84 is enlarged to include the pixels of expanded stool group $S_E$ (i.e., those pixels within the expansion distance threshold D which have intensity values greater than −500 HU.

Other edge expansion algorithms can also be used. In another embodiment of the invention, for example, the initially identified perimeter 92 is expanded to include all pixels within the expansion distance threshold which have intensity values greater than the air intensity threshold value. Recursive image processing methodologies can be used to implement this and other edge expansion algorithms.

With reference back to FIG. 2, following the completion of marked stool identification step 56, the images are processed to remove the identified marked stool 84 within the edge expanded perimeter 92 as shown in FIG. 6. In one embodiment of the invention, the marked stool 84 is replaced with pixel intensity values representing air. The marked stool can also be replaced with other image features in accordance with the preferences of the radiologist that will be performing diagnoses using the images. For example, when processed in three-dimensional form, the identified stool can be replaced with the colon wall 80, polyps or other features that may be present in the field of view behind the marked and removed stool 84.

Figure 10:
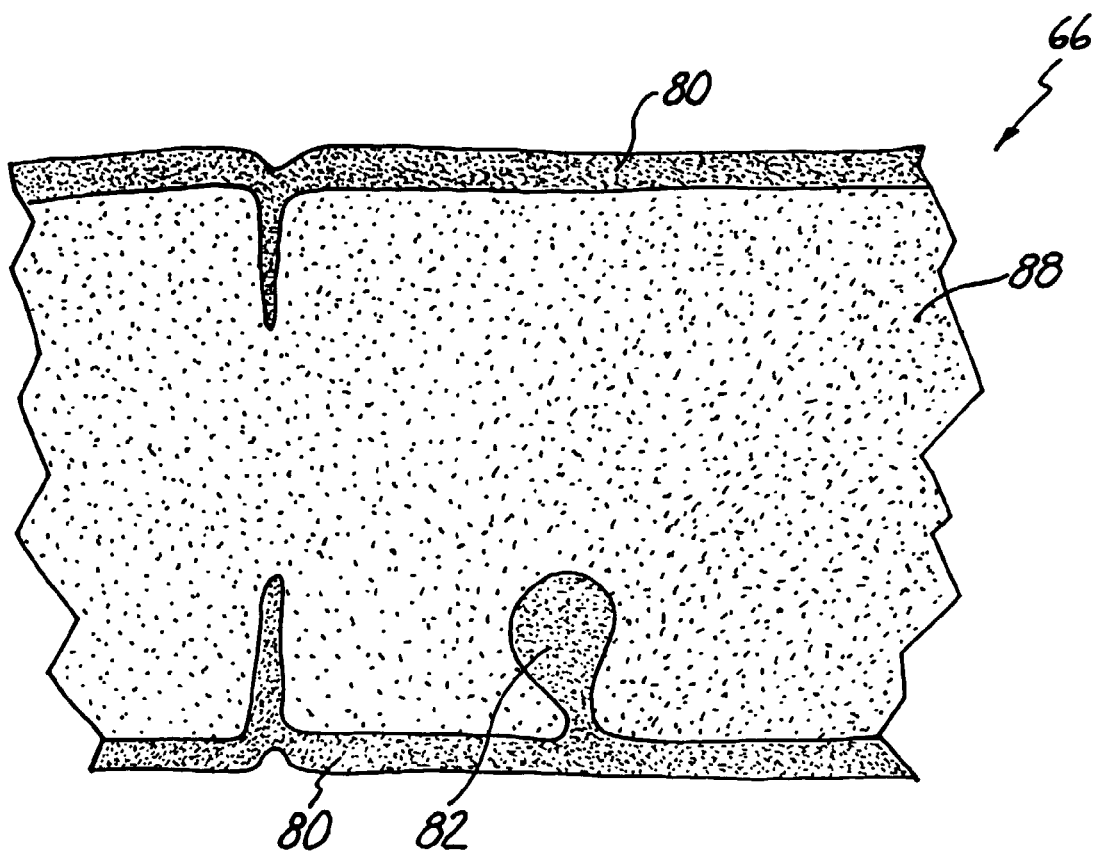
FIG. 10 is an image of the portion of the colon shown in FIG. 6 following the removal of the identified stool.
Figure 11:
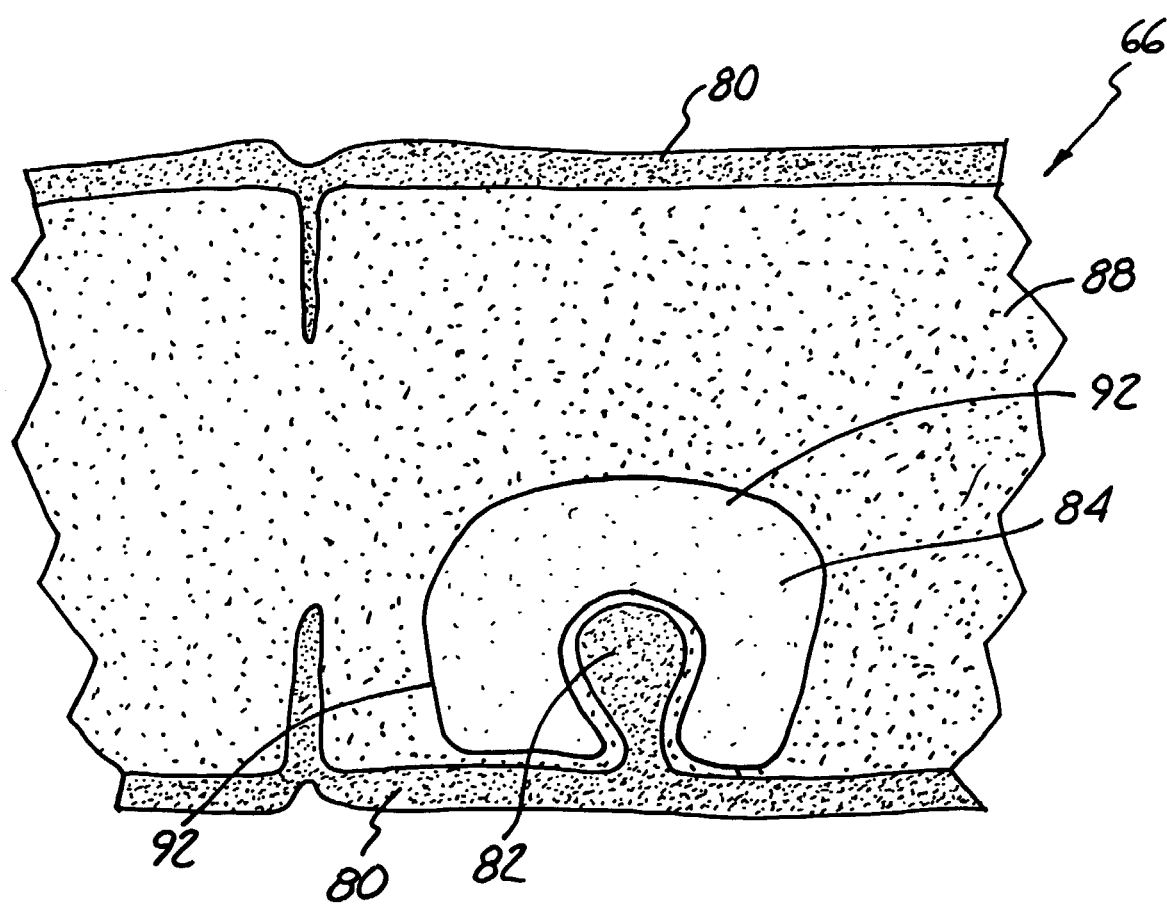
FIG. 11 is an image of the portion of the colon shown in FIG. 6 showing the stool as it would appear if not marked in accordance with the present invention.

FIG. 10 is an illustration of the image corresponding to that in FIG. 8 after the marked stool 84 has been removed and replaced with pixel intensity values corresponding to air 88. For purposes of comparison, FIG. 11 is an illustration of an image corresponding to that in FIG. 8 in which the stool 84 has not been marked. As shown in FIG. 11, it can be difficult to visually distinguish the unmarked stool 84 from the polyp 82 since they have similar densities in the image. Residual stool 84 in the colon 66 can therefore mask the presence of polyps 82, reducing the efficacy of colorectal screening procedures. After the stool 84 has been virtually removed from the image, polyps such as 82 that might have been masked are generally more readily identified.

Image processing techniques for implementing the stool identification and removal steps 56 and 58, respectively, described above, are generally known. Any conventional or otherwise known techniques for performing the functions of the described steps 56 and 58 can be used to implement the invention. Also, although the tests described below were performed using images processed in two-dimensional form, the steps 56 and 58 can be implemented in three-dimensional form as well using similar image processing techniques. Use of the invention in three-dimensional form can also offer enhanced efficacy. For example, the feature identified as the island of unmarked stool 86 (FIG. 6) using the two-dimensional processing form described above could be the end of a polyp which is connected to the colon wall. Application of the invention in three-dimensional form could identify such a feature as a polyp under these circumstances since it would not meet the removal criterion of step 72 (i.e., is not completely surrounded by marked stool).

Figure 24A:
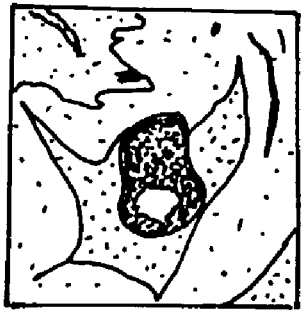
FIG. 24A is a two-dimensional CT image of portion of a colon which includes a section of stool marked in accordance with the present invention.
Figure 24B:
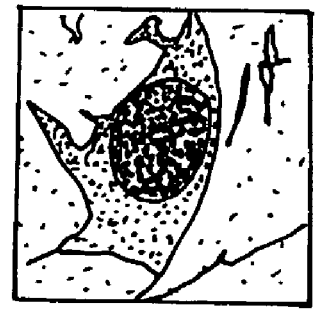
FIG. 24B is a two-dimensional CT image of the same portion of the colon shown in FIG. 24A, from which the section of marked stool has been removed in accordance with the present invention.
Figure 25A:
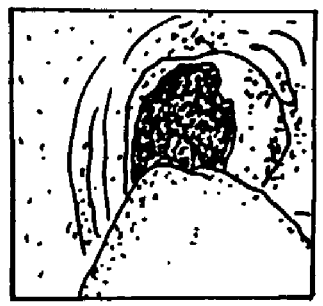
FIG. 25A is a three-dimensional CT image of portion of a colon which includes a section of stool marked in accordance with the present invention.
Figure 25B:
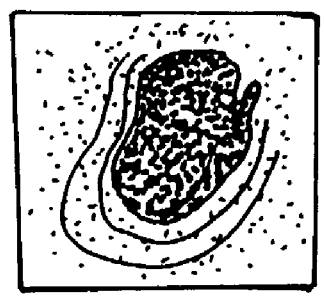
FIG. 25B is a three-dimensional CT image of the same portion of the colon shown in FIG. 25A, from which the section of marked stool has been removed in accordance with the present invention.

After the set colonography images are generated in the manner described above, they are displayed to a radiologist for diagnosis as shown by step 60 in FIG. 2. The colonography images can be displayed to the radiologist in any conventional or otherwise known manner preferred by the radiologist. By way of example, a variety of image display approaches that can be used for this purpose are described in the patent documents referenced in the Background of the Invention section above. FIG. 24A is a two-dimensional CT image of portion of a colon image of the same portion of the colon shown in FIG. 24A, from which the section of marked stool has been removed in accordance with the method described above. FIG. 25A is a three-dimensional CT image of portion of a colon which includes a section of stool marked in accordance with the present invention. FIG. 25B is a three-dimensional CT image of the same portion of the colon shown in FIG. 25A, from which the section of marked stool has been removed in accordance with the present invention.

A comprehensive test of the invention was performed on a study group population including 32 male and 25 female patients, all of whom were known or suspected to have colorectal polyps or colon cancer. The referral sources were conventional barium enema exams, flexible sigmoidoscopy exams and colorectal surgery. The study population was divided into 5 groups. The study protocol called for the patients of each group to be administered 225 ml (7.5 oz) doses of suspended barium sulfate solution over a range of time schedules. The barium sulfate solution was obtained from Medefield Pty Ltd of Artarmon NSW, Australia. The barium sulfate solution was similar to the company's MedeScan barium oral contrast solutions, with the amount of barium reduced to 1.2% and reduced levels of suspension agents. This barium sulfate solution was found to produce reduced levels of streaks and artifacts in the image, as well as minimizing coating of the colon.

Figure 13:
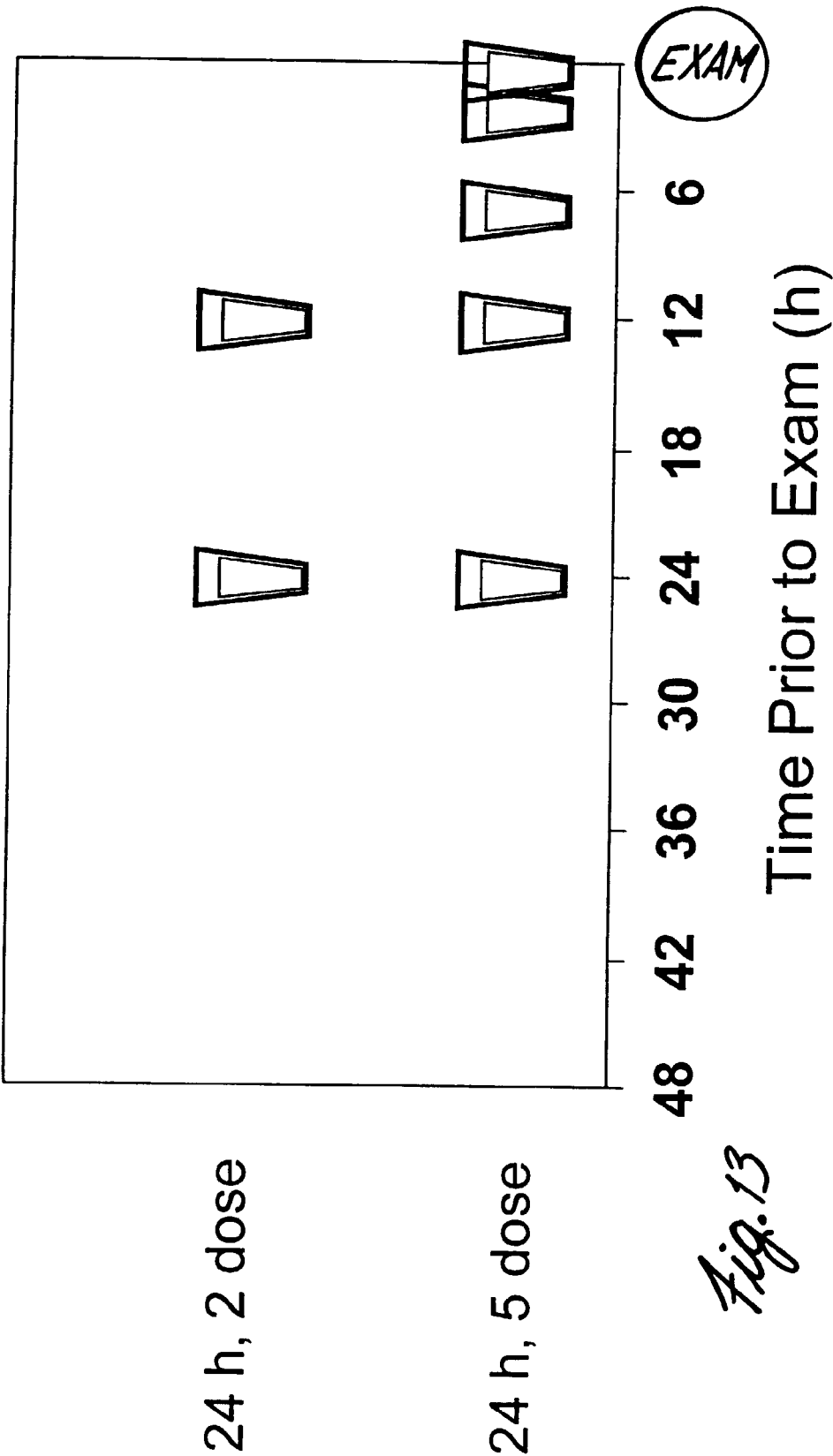
FIG. 13 is a chart describing and illustrating in detail the administration schedule for the groups of patients that received doses of suspended barium sulfate over 24 hour periods.
Figure 14:
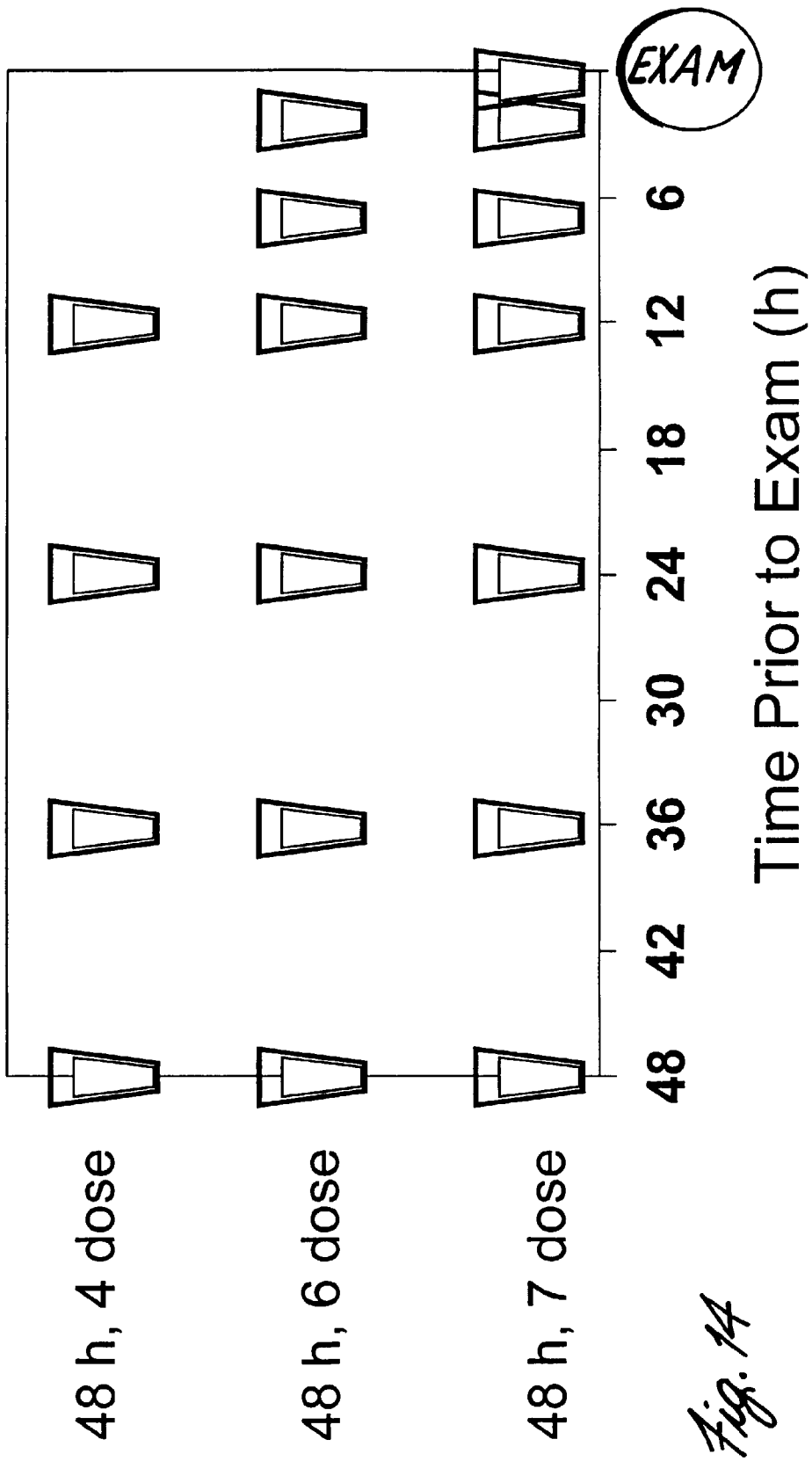
FIG. 14 is a chart describing and illustrating in detail the administration schedule for the groups of patients that received doses of suspended barium sulfate over 48 hour periods.

FIG. 12 is a chart describing the barium sulfate administration schedule for of the 5 groups, and the number of patients (No. pts) in each group. As shown, the period of administration ranged from 24 to 48 hours prior to imaging, while the total number of doses administered ranged from 2 to 7. FIG. 13 is a detailed description of the timing of the administration for the two groups of patients that received the doses over a 24 hour period. FIG. 14 is a detailed description of the timing of the administration for the three groups of patients that received the doses over a 48 hour period.

As noted above, the imaging for the test was performed on a commercially available General Electric Light Speed model CT scanner. The imager was configured for multislice operation at 50 mA, 5 mm slice thickness, 3 mm reconstruction intervals, HQ mode and 15 mm/rotation table speed. The colons of all patients were insufflated with air. Images were taken with the patients in both the prone and supine images. The images were presented to the radiologists in the formats described in PCT publication WO 98/32371. No cathartics were administered to the patient prior to the imaging.

With the marked stool threshold value set to 150 HU, the colonography images from each patient of each group were assigned a score between 1 and 4 to describe the extent or degree by which the associated barium sulfate suspension administration protocol was effective at labeling or marking stool present within the colons of the associated patients. FIG. 15 is an illustration of the scoring system, with the listed percentage range being the amount of stool in the colons that was adequately marked by the associated protocol. Individual scores were assigned for each section (cecum, right, transverse, left, sigmoid and rectum) of the colon.

Figure 18:
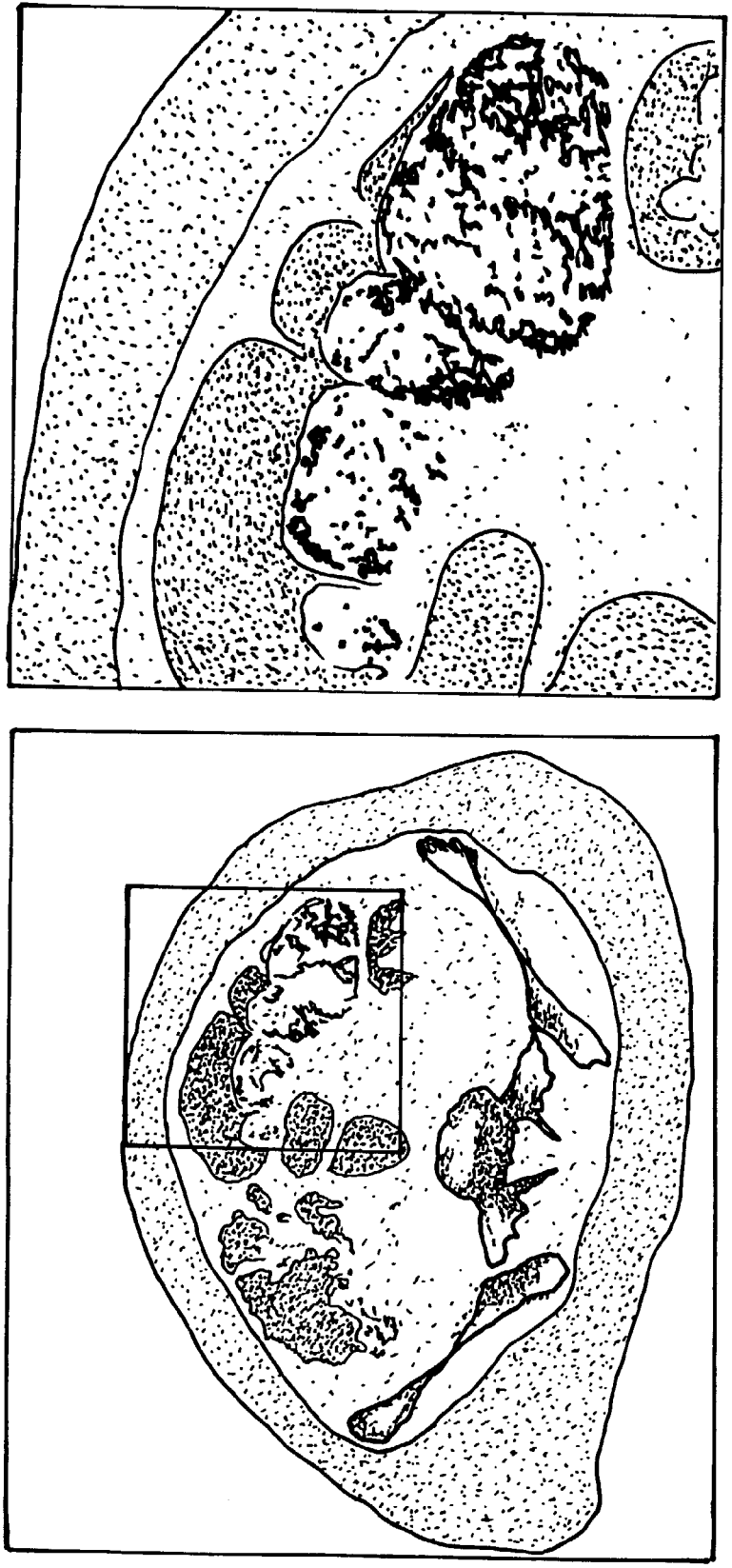
FIG. 18 is a CT image of a cross section of an abdomen including portions of a colon, and a detailed CT image of a portion of the colon, illustrating an example of the type of stool marking that would be assigned a score of 2 in the test.
Figure 19:
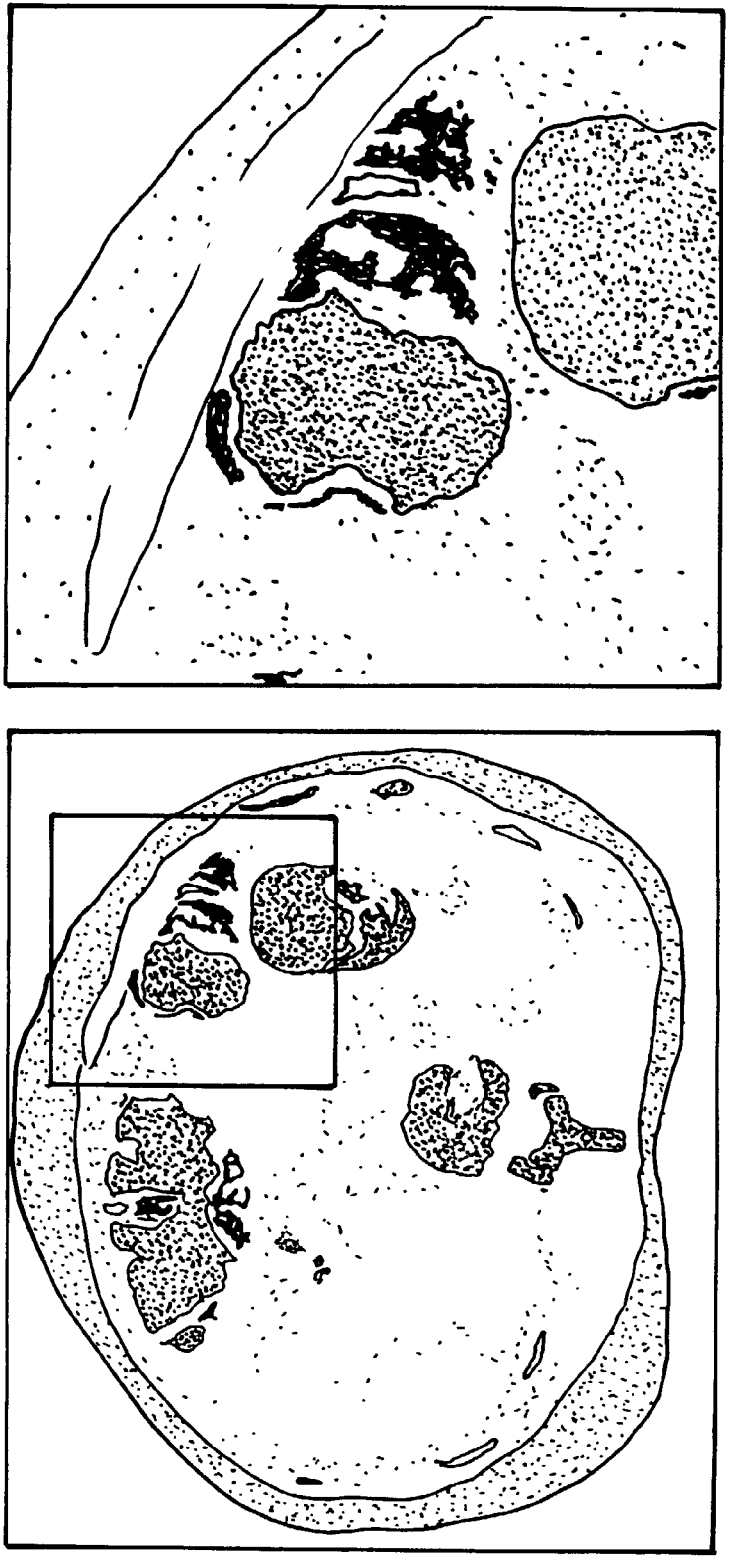
FIG. 19 is a CT image of a cross section of an abdomen including portions of a colon, and a detailed CT image of a portion of the colon, illustrating an example of the type of stool marking that would be assigned a score of 3 in the test.

FIG. 16 is a CT image of a cross section of an abdomen including portions of a colon, and a detailed CT image of a portion of the colon, illustrating an example of the type of stool marking that would be assigned a score of 0 in the test. FIG. 17 is a CT image of a cross section of an abdomen including portions of a colon, and a detailed CT image of a portion of the colon, illustrating an example of the type of stool marking that would be assigned a score of 1 in the test. FIG. 18 is a CT image of a cross section of an abdomen including portions of a colon, and a detailed CT image of a portion of the colon, illustrating an example of the type of stool marking that would be assigned a score of 2 in the test. FIG. 19 is a CT image of a cross section of an abdomen including portions of a colon, and a detailed CT image of a portion of the colon, illustrating an example of the type of stool marking that would be assigned a score of 3 in the test. FIG. 20 is a CT image of a cross section of an abdomen including portions of a colon, and a detailed CT image of a portion of the colon, illustrating an example of the type of stool marking that would be assigned a score of 4 in the test.

Figure 21:
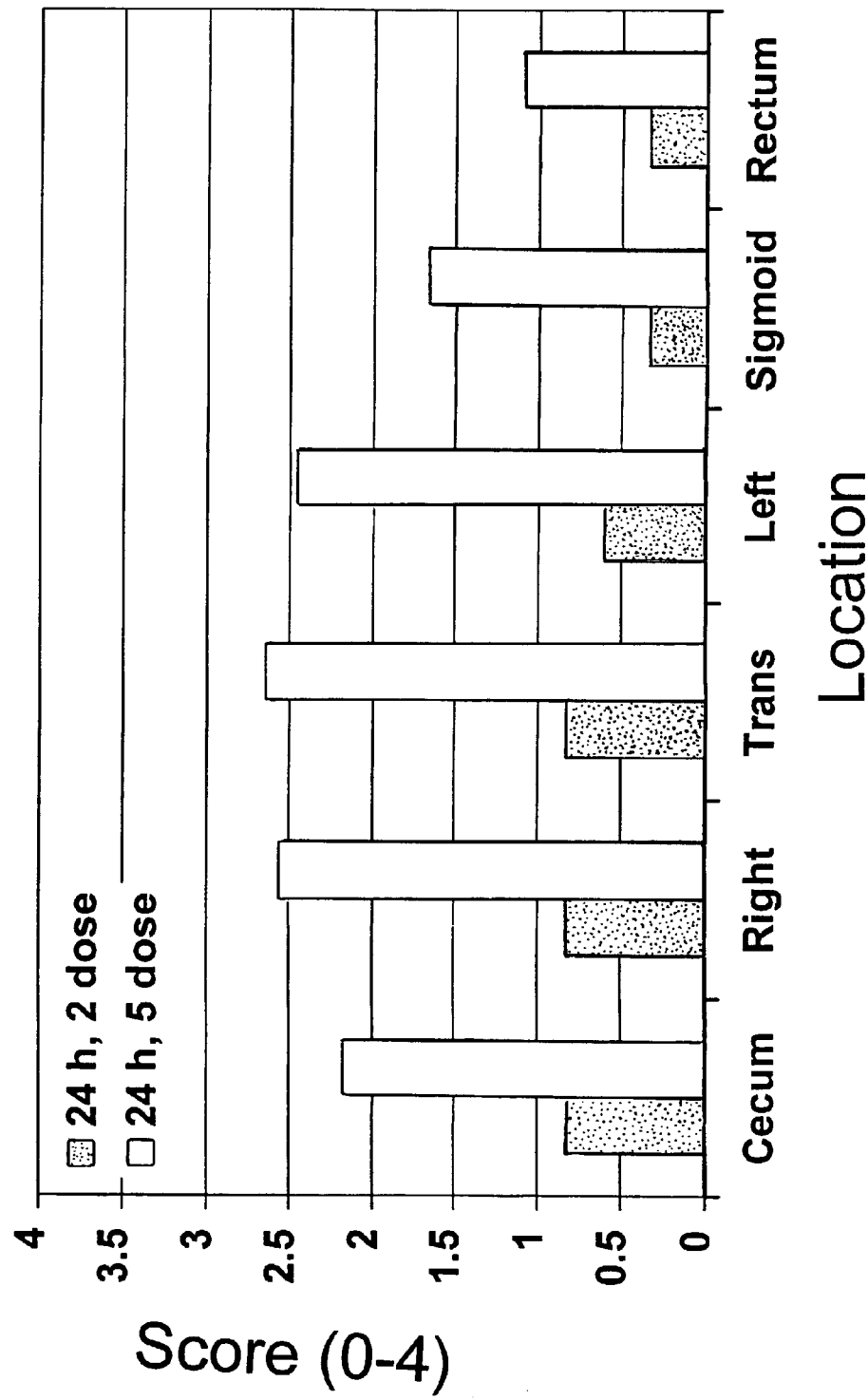
FIG. 21 is a graph of the stool labeling efficacy obtained from the two groups of patients administered doses of barium sulfate suspension over a 24 hour period in the test.
Figure 22:
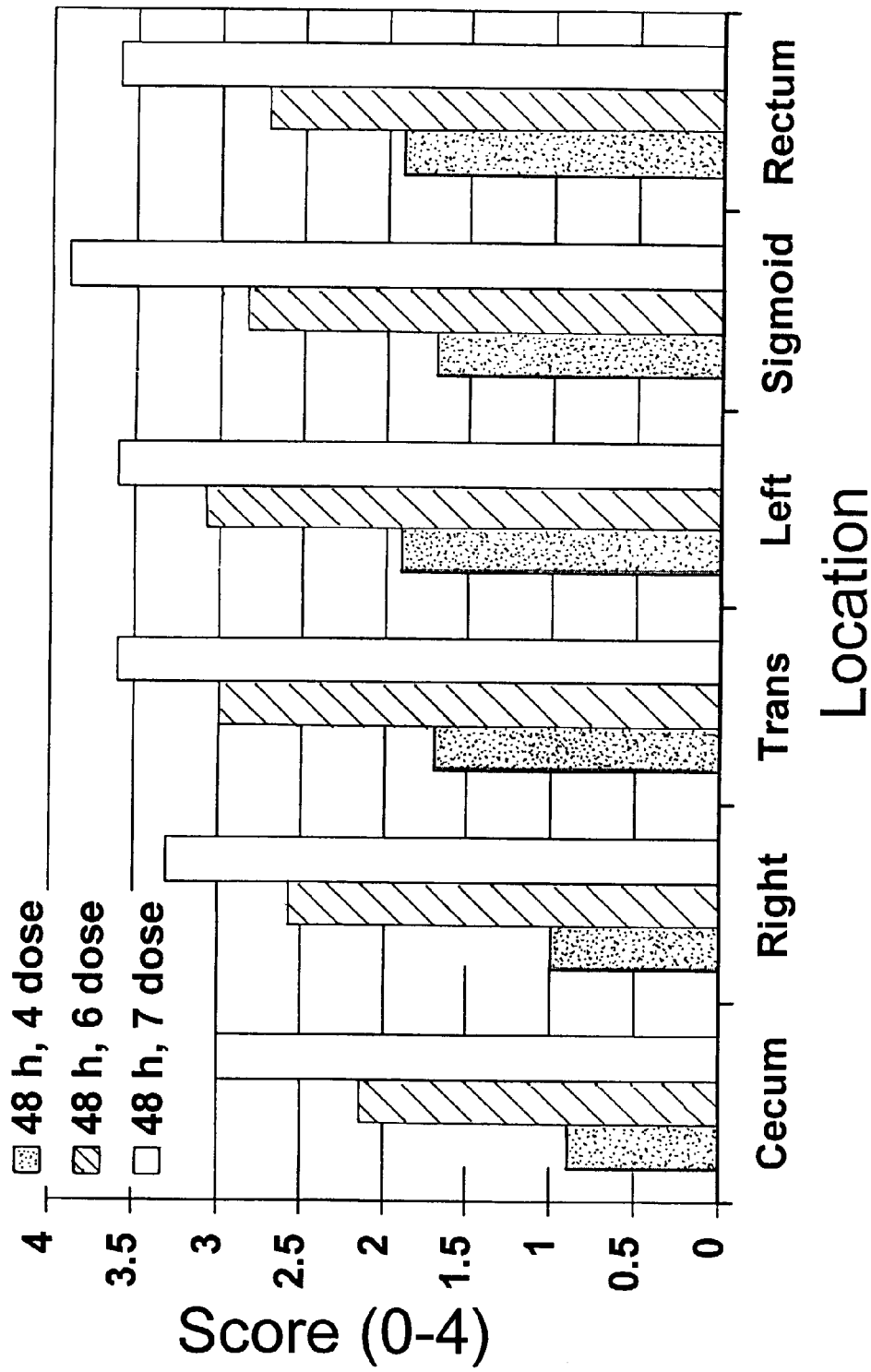
FIG. 22 is a graph of the stool labeling efficacy obtained from the two groups of patients administered doses of barium sulfate suspension over a 48 hour period in the test.
Figure 23:
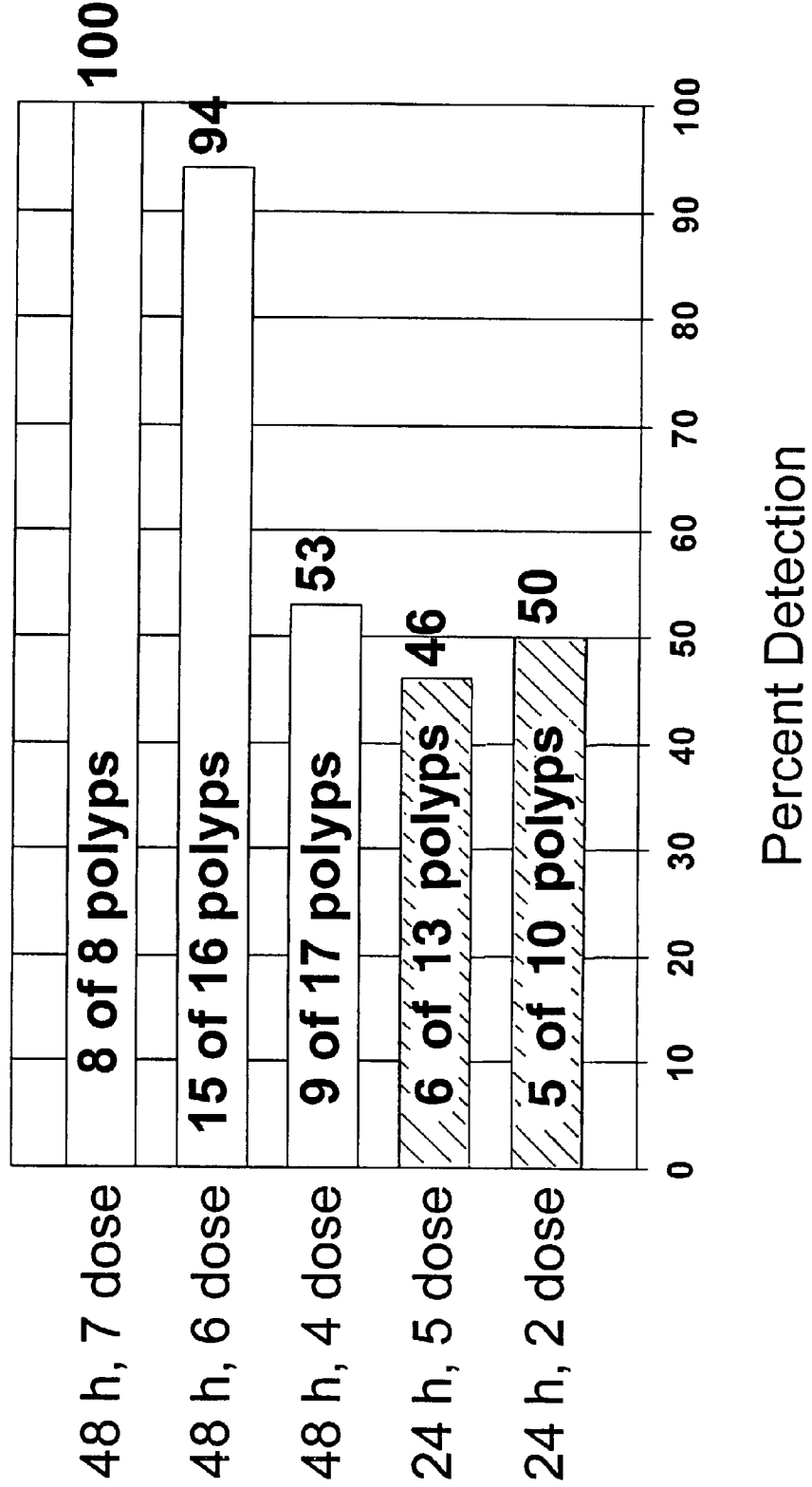
FIG. 23 is a graph of the polyp detection results obtained from the images generated during the test.

FIG. 21 is a graph of the stool labeling efficacy obtained from the two groups of patients administered doses of barium sulfate suspension over a 24 hour period. A separate score is provided for each of the sections of the colon. FIG. 22 is a graph of the stool labeling efficacy obtained from the three groups of patients administered doses of barium sulfate suspension over a 48 hour period. Again, a separate score is provided for each of the sections of the colon. From the test results illustrated in FIGS. 21 and 22 it is evident that orally administered barium sulfate suspensions are capable of mixing with stool throughout the colon to a level which is sufficient to enable the stool to be identified and both visually and electronically discriminated from other colon tissues. It appears from this test data that the quality of the stool marking (i.e., the test scores) is more closely related to the quantity of the stool marker administered to the patient than to the length of time over which the marker was administered. It also appears that the administration of stool marker at times relatively close to the imaging procedure (e.g., within 6 hours of the exam) also enhanced the quality of the stool marking.

FIG. 22 is a chart describing the percent of polyps that were detected on the basis of a review of the colonography images for each of the study groups. The percentage of detection was especially high in the study groups that were administered the barium sulfate suspension over 48 hour periods. On the basis of these tests it is evident that the detection of polyps less than or equal to 1 cm is possible with a relatively high degree of sensitivity. This sensitivity is similar to that reported using conventional colonography techniques on a fully prepared colon.

Another test similar to that described above was conducted using powdered or flaked barium administered to the patients in pill (capsule) form. One group of patients in this test received capsules filled with 600 mg of commercially available Barosperse. Another group of patients in the test received capsules filled with 600 mg of commercially available USP barium. Both groups of patients were administered 3 pills with all three meals and at bedtime during the two days preceding the imaging procedure and three pills the morning of the imaging procedure (i.e., a total of twenty seven 600 mg pills). An 8 oz dose of 2.0% liquid barium suspension was also administered orally 30–60 minutes prior to the imaging procedure. The results of the test in terms of stool labeling scoring and percentage of polyp detection for both groups of patients was similar to the results obtained with the group of patients that were administered 7 doses of barium sulfate suspension over the 48 hour period before the imaging procedure.

The virtual colon preparation and colonography technique of the present invention offers important advantages. In particular, it is very convenient and efficient to implement, and will therefore result in enhanced patient acceptance and compliance. Furthermore, the methodology is capable of producing highly efficacious diagnoses.

Although the present invention has been described with reference to preferred embodiments, those skilled in the art will recognize that changes can be made in form and detail without departing from the spirit and scope of the invention. In particular, although it can be advantageous to simulate colon cleansing by electronically removing the marked stool, efficacious colorectal cancer screening diagnoses can also be made through visual observations of the colonography images with the marked stool present. This is especially the case when the stool is thoroughly marked, and the visual characteristics of the marked stool are clearly distinguishable from those of the soft tissues. Also, other image processing techniques can be used to identify the marked stool within the colon. Furthermore, although the present invention can be used in connection with an unprepared colon, it can also enhance the efficacy of colonography diagnostic procedures performed on patients that have followed conventional preparation processes to varying degrees. In general, the less stool in the colonography images, even if marked in accordance with this invention, the less the likelihood that polyps or other tissues of interest to a radiologist will be masked by the stool.

What is claimed is:

1. A method for imaging a patient's unprepared colon for colorectal screening, comprising:
   prescribing the administration of at least about 10 grams of stool marker in doses to the patient over at least a 48 hour administration period including at least 1 dose of stool marker less than about 2 hours before imaging the colon; and
   with the patient free from colon preparation, including from the administration of laxatives or cathartics, for at least 24 hours, imaging the patient's colon after the administration period.

2. The method of claim 1 and further including displaying the images.

3. The method of claim 1 wherein prescribing the administration of stool marker includes prescribing the administration of a pill including stool marker.

4. The method of claim 1 wherein prescribing the administration of doses of barium stool marker includes prescribing the administration of doses of barium sulfate suspension including between about 0.8% and 1.5% barium.

5. The method of claim 1 and further including producing and displaying images of the patient's colon.

6. A method for imaging a patient's unprepared colon for colorectal screening, comprising:
   prescribing the administration of doses of stool marker to the patient over at least a 24 hour administration period, including at least 3 doses of stool marker less than about 7 hours before the end of the administration period; and
   with the patient free from administration of laxatives or cathartics for at least 24 hours, imaging the patient's colon after the administration period.

7. The method of claim 6 wherein prescribing the administration of at least 3 doses of stool marker less than about 7 hours before the end of the administration period includes prescribing the administration of at least 2 doses of stool marker less than about 2 hours before the end of the administration period.

8. The method of claim 7 wherein prescribing the administration of stool marker includes prescribing the administration of barium stool marker.

9. The method of claim 8 wherein prescribing the administration of doses of barium stool marker includes prescribing the administration of doses of barium sulfate suspension including between about 0.8% and 1.5% barium.

10. The method of claim 9 wherein prescribing the administration of doses of barium stool marker include, prescribing the administration of pills including barium stool marker.

11. The method of claim 6 and further including displaying the images.

12. The method of claim 6 and further including producing and displaying images of the patient's colon.

13. A method for imaging a patient's unprepared colon for colorectal screening, comprising:
   prescribing the administration of doses of barium sulfate suspension stool marker to the patient over at least a 48 hour administration period, including at least 2 doses of stool marker less than about 6 hours before the end of the administration period, each dose including between about 0.8% and 1.5% barium sulfate; and
   with the patient free from administration of laxatives or cathartics for at least 24 hours, imaging the patient's colon after the administration period.

14. The method of claim 13 wherein prescribing the administration of doses of barium stool marker includes prescribing the administration of pills including the barium stool marker.

15. The method of claim 13 and further including displaying the images.

16. The method of claim 13 and further including producing and displaying images of the patient's colon.

17. A method for imaging a patient's unprepared colon for colorectal screening, comprising:
   prescribing the administration of at least about 10 grams of stool marker in doses to the patient over at least a 48 hour administration period, including prescribing the administration of at least three doses of stool marker over the administration period, including at least two doses of stool marker less than about six hours before imaging the colon; and
   with the patient free from colon preparation, including from the administration of laxatives or cathartics, for at least 24 hours, imaging the patient's colon after the administration period.

18. The method of claim 17 and further including displaying the images.

19. The method of claim 17 wherein prescribing the administration of stool marker includes prescribing the administration of a pill including stool marker.

20. The method of claim 17 wherein prescribing the administration of doses of barium stool marker includes prescribing the administration of doses of barium sulfate suspension including between about 0.8% and 1.5% barium.

* * * * *